| United States Patent [19] | [11] Patent Number: 5,441,703 |
|---|---|
| Jürgensen | [45] Date of Patent: Aug. 15, 1995 |

[54] GAS INLET FOR A PLURALITY OF REACTANT GASES INTO REACTION VESSEL

[75] Inventor: Holger Jürgensen, Aachen, Germany

[73] Assignee: Aixtron GmbH, Germany

[21] Appl. No.: 219,415

[22] Filed: Mar. 29, 1994

Related U.S. Application Data

[63] Continuation of Ser. No. 41,347, Apr. 1, 1993, abandoned, which is a continuation of Ser. No. 911,366, Jul. 13, 1992, abandoned, which is a continuation of Ser. No. 652,400, Feb. 7, 1991, abandoned, which is a continuation of Ser. No. 334,701, filed as PCT/DE88/00399, Jun. 30, 1988, abandoned.

[30] Foreign Application Priority Data

Jun. 30, 1987 [DE] Germany .................. 37 21 637.6

[51] Int. Cl.⁶ .................. B05B 7/00; B05B 7/04
[52] U.S. Cl. .................. 422/129; 239/400; 239/428; 239/432
[58] Field of Search ......... 422/129; 239/400, 428, 239/432, 434; 118/715; 156/345, 643; 55/462, 463

[56] References Cited

U.S. PATENT DOCUMENTS

| 598,630 | 2/1898 | Iler | 55/462 |
|---|---|---|---|
| 2,205,336 | 6/1940 | Beach | 55/462 |
| 4,002,432 | 1/1977 | Brice | 55/462 |
| 4,141,701 | 2/1979 | Ewan et al. | 55/90 |

FOREIGN PATENT DOCUMENTS

| 0648275 | 12/1928 | France . | |
|---|---|---|---|
| 0493645 | 2/1930 | Germany | 55/462 |
| 0064069 | 5/1977 | Japan | 55/462 |
| 1037863 | 2/1980 | Japan | 422/129 |
| 62-33516 | 2/1987 | Japan | 55/462 |
| 0110397 | 6/1966 | Netherlands . | |
| 1210884 | 2/1986 | U.S.S.R. | 422/129 |
| 1329801 | 8/1987 | U.S.S.R. | 55/462 |

OTHER PUBLICATIONS

Capron, B. A., Herring, R. B., "Silicon Nitride Deposition in a Vertical Flow Reactor," *Extended Abstracts*, Oct. 1984, p. 738.

Gallagher, J. P., Li, P. C., "Gas Injector for Nitride Deposition Using 2% Silane Gas," *IBM Technical Disclosure Bulletin*, Dec. 1983.

Perry & Chilton, *Chemical Engineer's Handbook*, 5th Ed. pp. 18-61-18-62.

Primary Examiner—Robert J. Warden
Assistant Examiner—Robert Carpenter
Attorney, Agent, or Firm—Evenson, McKeown, Edwards & Lenahan

[57] ABSTRACT

A gas inlet for different reactant gases which flow into reaction vessels with high flow velocity. The cross sections of the gas inlet supply lines are substantially smaller than that of the reaction vessel.

The gas inlet has a part with a conicoidal interior contour, the cross section of which is adapted to the cross section of the reaction vessel and which is arranged at one end of the reaction vessel through which flow occurs. The individual supply lines end at approximately the focal point of the part having the conicoidal interior contour. The gas exit openings of the supply lines are directed at the vertex of the part having the conicoidal interior contour.

2 Claims, 1 Drawing Sheet

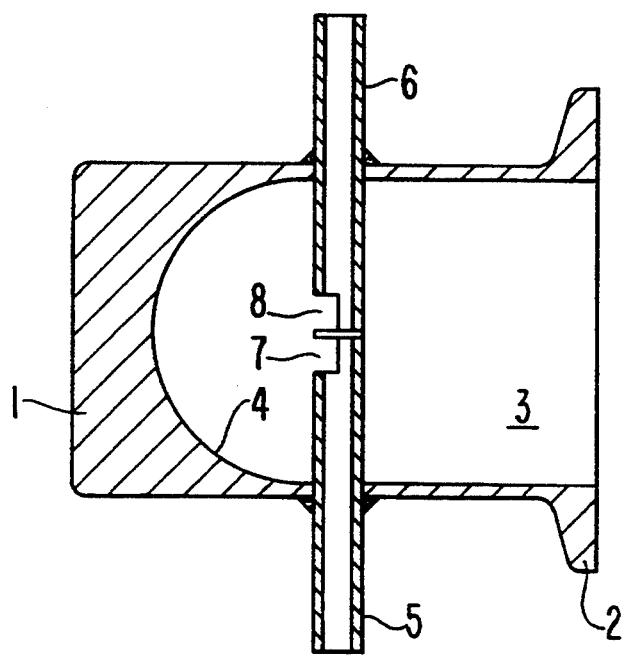

GAS INLET FOR A PLURALITY OF REACTANT GASES INTO REACTION VESSEL

This is a continuation of application Ser. No. 08/041,347, filed Apr. 1, 1993, now abandoned, which is a continuation of application Ser. No. 07/911,366, filed Jul. 13, 1992, now abandoned, which is a continuation of application Ser. No. 07/652,400, filed Feb. 7, 1991, now abandoned, which is a continuation of application Ser. No. 07/334,101, filed as PCT/DE88/00399, Jun. 30, 1988, now abandoned.

BACKGROUND AND SUMMARY OF THE INVENTION

The present invention relates to a gas inlet for different reactant gases which flow into reaction vessels with high flow velocity, and having supply lines whose cross sections are substantially smaller than that of the reaction vessel.

Gas inlets of this kind are needed, by way of illustration in MOCVD ( metal oxide chemical vapor deposition) reactors, but also in other reactors for the production of semi-conductors, whereby the general problem is that one or several gas flows led in via a supply line having a relatively small cross section should be widened to a large cross section as homogeneously as possible and with no dead volume. This is particularly significant if as "sharp" as possible boundaries are to be produced between the films by switching the gas flows.

An object of present invention is to improve a gas inlet for a majority of reactant gases into reaction vessels in such a manner that one or more gas flows can be widened to a relatively large cross section as homogeneously as possible with no dead volume.

An inventive feature is that the gas inlet has a part, the interior contour of which is conicoidal in shape, the cross section of which is adapted to the cross section of the reaction vessel and which is arranged at one end of the reaction vessel through which flow occurs. The individual supply lines end at approximately the focal point of the part having a conicoidal interior contour, whereby the gas exit openings of the supply lines are directed at the vertex of the conicoidal part.

Thus, the "thin" gas jet issuing with high velocity from the gas exit openings of the supply lines is widened homogeneously and with no dead volume with reflection off the conicoidal interior contour. An star-shaped arrangment of the supply lines permits the introduction of several types of gas (simultaneously and/or serially) without disturbing the homogeneity of the widened gas flow.

For practical purposes a more than sufficient homogeneity of the widened gas jet is yielded if the interior contour of the conicoidal part, i.e. the conicoidal shape, is approximated by a hemisphere.

As result of gas exit openings of the supply line atomization is achieved, and thereby further homogeneity of the gas flow via the cross section of the reactor is obtained.

Brief Description of the Drawing

The present invention is made more apparent in the following detailed description using a preferred embodiment with reference to the accompanying drawing, the sole figure of which shows a cross section of a gas inlet according to the present invention.

DESCRIPTION OF A PREFERRED EMBODIMENT

The gas inlet of the present invention has a basic body 1, on which is a flange 2. The flange 2 serves to connect the basic body 1 with a reactor (not illustrated herein), by way of illustration a reactor like the one described in the patent application "Quartz glass Reactor for MOCVD Systems" filed on the same date (German Application P 37 21 636.8, filed Jun. 30, 1987, PCT Application DE 88/00397).

The recess 3 provided in the basic body 1 has a rear end surface 4, the shape of which is hemispherical in the illustrated presently preferred embodiment.

Furthermore gas supply lines are provided, which are arranged in a star-shaped configuration and of which only two lines 5 and 6 are depicted in the drawing. The supply lines 5 and 6 are provided with exit openings 7 and 8 which are located approximately in the center of the hemispherical surface 4. The edges of the exit openings are broken in such a manner that the issuing gas jet is partially atomized.

The gas inlet according to the present invention operates as follows:

The gas flows issuing with high velocity from exit openings 7 or 8 are practically atomized by the structure of the edge of the openings and hit an area of the surface 4. The gas flow issuing with high velocity is reflected by this surface in such a manner that it is homogeneously widened and further atomized by the counter flow of the gas flow issuing from the openings 7 and 8 and exits through the opening of flange 2 in the reactor.

The present invention has been described in the preceding section using a preferred embodiment without the intention of limiting the scope or spirit of the overall inventive concept, within which there are, of course, are many most varied possible modifications.

Thus, by way of illustration, a conic section surface (conicoidal interior contour), for example a paraboloid, may be utilized instead of a spherical surface. In the present case, such further development of spherical surfaces known from geometric optics, however, yields only negligible advantages.

The number of gas inlet lines may be increased as desired. The star-shaped arrangement results in the same conditions for all gas flows and, in particular, a homogeneous gas distribution over the cross section.

Thus, the invented gas inlet is not only suited for serial introduction of different gas flows, which are supposed to be rapidly switched, but also for simultaneous introduction of several gases, which are supposed to be homogeneously widened and thoroughly mixed.

What is claimed is:

1. A gas inlet for flowing different reactant gases into a reaction vessel, comprising a hollow body having an exit opening arranged at one end of the reaction vessel and extending over a cross section of the hollow body, said hollow body also having a conicoidal interior contour at an end remote from the exit opening and the same free cross-section as the exit opening except for cross sections of the supply lines having gas exit openings and being arranged in relation to the conicoidal interior contour such that the gas exit openings of said supply lines are configured to partially spray and direct the different reactant gases toward the conicoidal interior contour so that a flow of different reactant gases toward the exit opening is homogeneously widened by the conicoidal interior contour and is further atomized by the flow of the different reactant gases from the supply lines.

2. A gas inlet according to claim 1, wherein said conicoidal shape is approximated by a hemisphere.

* * * * *